(12) United States Patent
Narula et al.

(10) Patent No.: US 7,384,897 B1
(45) Date of Patent: *Jun. 10, 2008

(54) CYCLOPROPANECARBONITRILE ANALOGUES AND THEIR USE IN PERFUME COMPOSITIONS

(75) Inventors: Anubhav P. S. Narula, Hazlet, NJ (US); Edward Mark Arruda, Cliffwood, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/689,822

(22) Filed: Mar. 22, 2007

(51) Int. Cl.
*C11D 3/50* (2006.01)
(52) U.S. Cl. ........................ 510/106; 512/22; 558/430; 558/434
(58) Field of Classification Search ............... 510/22; 512/22; 558/430, 434
See application file for complete search history.

(56) References Cited

U.S. PATENT DOCUMENTS

2006/0287204 A1* 12/2006 Narula et al. ............... 510/101

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention is directed to the novel cyclopropanated cyclohexyl ester compounds of the general formula:

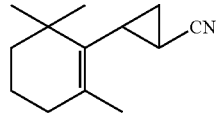

Structure I

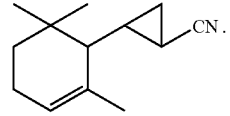

Structure II

28 Claims, No Drawings

CYCLOPROPANECARBONITRILE ANALOGUES AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

In the first embodiment of the invention, the novel compounds represented by the following structures are provided:

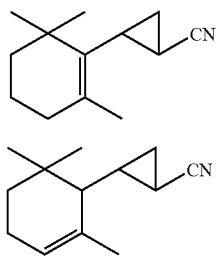

Structure I

Structure II

In another embodiment of the invention a method for enhancing a perfume composition by incorporating an olfactory acceptable amount of the Structure I is provided.

In another embodiment of the invention a method for enhancing a perfume composition by incorporating an olfactory acceptable amount of the Structure I is provided.

In a further embodiment a composition containing Structure I and II is provided and methods enhancing a perfume composition by incorporating an olfactory acceptable amount of the Structure I and Structure II.

These and other embodiments of the present invention will be apparent by reading the following specification.

DETAILED DESCRIPTION OF THE INVENTION

Those with the skill in the art will appreciate that the compound of Structure I-(2,6,6-Trimethyl-1-cylohexen-1-yl)-cyclopropanecarbonitrile and Structure II is 2-(2,6,6-Trimethyl-2-cylohexen-1-yl)-cyclopropanecarbonitrile.

The compounds of the present invention may be prepared from the corresponding compounds via a Corey's cyclopropanation reaction of the following sequence:

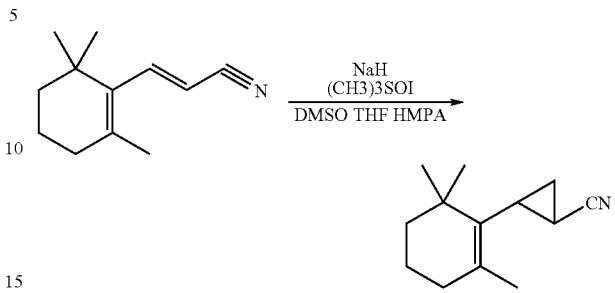

The starting materials for the above reaction are commercially available from Aldrich. According to the present invention, DMSO is represents dimethyl sulfoxide, THF stands for tetrahydrofuran and HMPA stands for hexamethylphosphoramide.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have discovered that the fragrance notes of Structures I and II are vetiver, complex citrus, mandarin, calone, roseoxide, slightly animalic and leathery, sweet, herbal and woody in odor and are well suited for use as a fragrance ingredient. In a more preferred embodiment, a composition of Structure I and Structure II is provided in a ratio from about 2 parts to about 1 part by weight.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honey-suckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE A

Preparation of cyclopropanecarbonitrile 2-(2,6,6-trimethyl-1-cylohexen-1-yl)- and cyclopropanecarbonitrile 2-(2,6,6-trimethyl-2-cyclohexen-1-yl)-

To a dry 2 L multi-neck round bottom flask fitted with an air stirrer, a nitrogen inlet condenser and an additional funnel, 24.7 g of $(CH_3)_3SOI$ (trimethyl sulfoxonium iodide), 40 g of anhydrous DMSO (dimethyl sulfoxide), 40 g of THF (tetrahydrofuran) and 1.5 g of HMPA (hexamethylphosphoramide) were charged and stirred. 5 g of sodium hydride was then added slowly to the reaction mixture and heated to 50° C. until $H_2$ bubbling stopped. 17.5 g of cyclocitrilidene acetonitrile was thereafter added. A sample was taken until maximum conversion. The mixture was cooled and quenched with 100 ml of cold water and 100 ml toluene. The aqueous layer was extracted with toluene (50 ml×3), which was then added to the organic layer and concentrated in a vacuum to produce crude which was distilled to provide the cyclopropanated product.

The odor was described as having vetiver, complex citrus, mandarin, calone, roseoxide, slightly animalic and leathery, sweet, herbal and woody fragrance notes.

The NMR of cyclopropanecarbonitrile, 2-(2,6,6-trimethyl-2-cyclohexen-1-yl)- is as follows:

0.9 ppm (s, 4H); 0.95 ppm (s, 1H); 1.0 ppm (d, 3H); 1.1 ppm (d, 6H); 1.2 ppm (d, 4H); 1.3 ppm (m, 1H); 1.4 ppm (m, 3H); 1.5 ppm (m, 1H); 1.6 ppm (m, 2H); 1.7 ppm (d, 1H); 1.8 ppm (s, 3H); 1.9 ppm (s, 2H); 2.1 ppm (m, 3H); 2.3 ppm (m, 3H); 2.5 ppm (m, 1H).

EXAMPLE B

Incorporation of 2-(2,6,6-trimethyl-1-cylohexen-1-yl)-cyclopropanecarbonitrile and 2-(2,6,6-trimethyl-2-cylohexen-1-yl)-cyclopropanecarbonitrile into a fragrance formulation

| | |
|---|---|
| Aldehyde AA 10% | 2 |
| Allyl Amyl Glycolate | 3 |
| Bacdanol | 10 |
| Bergamot Oil Colorless MD Lmr | 40 |
| Dihydro Iso Jasmonate | 150 |
| Galaxolide 50 | 170 |
| Helional | 10 |
| Hexenyl Salicylate, Cis-3 | 40 |
| Hexyl Salicylate | 30 |
| Iso E Super | 250 |
| Lemon Oil Italian | 5 |
| Lyral | 20 |
| Methyl Ionone Gamma | 10 |
| Pimento Berry Oil | 2 |
| Sage Oil | 3 |
| Styralyl Acetate | 5 |
| Cyclopropanecarbonitrile, 2-(2,6,6-Trimethyl-2-Cyclohexen-1-yl)- | 250 |
| Total | 1000 |

What is claimed is:

1. A compound of formula

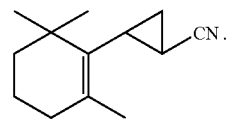

2. A method of improving, enhancing or modifying a fragrance formulation through the addition of an olfactory acceptable amount of the compound of claim 1.

3. The method of claim 2, wherein the fragrance formulation is incorporated into a product selected from the group consisting of perfumes, colognes, toilet waters, cosmetic products, personal care products, fabric care products, cleaning products and air fresheners.

4. The method of claim 3, wherein the cleaning products are selected from the group consisting of detergents, dishwashing compositions, scrubbing compounds and window cleaners.

5. The method of claim 2, wherein the amount incorporated into the fragrance formulation is from about 0.005 to about 10 weight percent.

6. The method of claim 2, wherein the amount incorporated into the fragrance formulation is from about 0.5 to about 8 weight percent.

7. The method of claim 2, wherein the amount incorporated into the fragrance formulation is from about 1 to about 7 weight percent.

8. A fragrance formulation containing an olfactory effective amount of the compound of claim 1.

9. A fragrance product containing the compound of claim 1.

10. A compound of formula

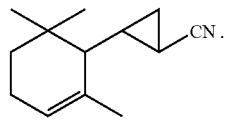

11. A method of improving, enhancing or modifying a fragrance formulation through the addition of an olfactory acceptable amount of the compound of claim 10.

12. The method of claim 11, wherein the fragrance formulation is incorporated into a product selected from the group consisting of perfumes, colognes, toilet waters, cosmetic products, personal care products, fabric care products, cleaning products and air fresheners.

13. The method of claim 12, wherein the cleaning products are selected from the group consisting of detergents, dishwashing compositions, scrubbing compounds and window cleaners.

14. The method of claim 11, wherein the amount incorporated into the fragrance formulation is from about 0.005 to about 10 weight percent.

15. The method of claim 11, wherein the amount incorporated into the fragrance formulation is from about 0.5 to about 8 weight percent.

16. The method of claim 11, wherein the amount incorporated into the fragrance formulation is from about 1 to about 7 weight percent.

17. A fragrance formulation containing an olfactory effective amount of the compound of claim 10.

18. A fragrance product containing the compound of claim 10.

19. A composition comprising

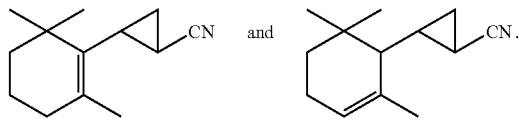

20. The composition of claim 19, wherein the weight ratio of

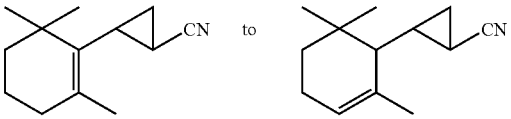

is from about 2 to about 1.

21. A fragrance product containing the composition of claim 19.

22. A method of improving, enhancing or modifying a fragrance formulation through the addition of an olfactory acceptable amount of the composition of claim 19.

23. The method of claim 22, wherein the fragrance formulation is incorporated into a product selected from the group consisting of perfumes, colognes, toilet waters, cosmetic products, personal care products, fabric care products, cleaning products and air fresheners.

24. The method of claim 23, wherein the cleaning products are selected from the group consisting of detergents, dishwashing compositions, scrubbing compounds and window cleaners.

25. The method of claim 22, wherein the amount incorporated into the fragrance formulation is from about 0.005 to about 10 weight percent.

26. The method of claim 22, wherein the amount incorporated into the fragrance formulation is from about 0.5 to about 8 weight percent.

27. The method of claim 22, wherein the amount of incorporated into the fragrance formulation is from about 1 to about 7 weight percent.

28. A fragrance formulation containing an olfactory effective amount of

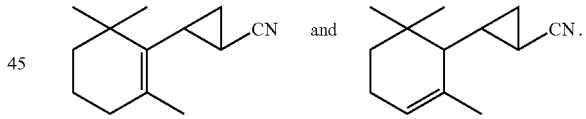

* * * * *